(12) United States Patent
Bai

(10) Patent No.: US 10,214,735 B2
(45) Date of Patent: Feb. 26, 2019

(54) **HEPARINASES OBTAINED FROM *SPHINGOBACTERIUM DAEJEONENSE*, PREPARATION THEREFOR AND APPLICATION THEREOF**

(71) Applicant: SHENZHEN HEPALINK PHARMACEUTICAL GROUP CO., LTD., Guangdong (CN)

(72) Inventor: Jiake Bai, Guangdong (CN)

(73) Assignee: Shenzhen Hepalink Pharmaceutical Group Co., Ltd., Guangdong (CN)

( * ) Notice: Subject to any disclaimer, the term of this patent is extended or adjusted under 35 U.S.C. 154(b) by 0 days.

(21) Appl. No.: 15/555,040

(22) PCT Filed: May 25, 2015

(86) PCT No.: PCT/CN2015/079704
§ 371 (c)(1),
(2) Date: Aug. 31, 2017

(87) PCT Pub. No.: WO2016/138700
PCT Pub. Date: Sep. 9, 2016

(65) Prior Publication Data
US 2018/0051270 A1    Feb. 22, 2018

(30) Foreign Application Priority Data

Mar. 5, 2015  (CN) .......................... 2014 1 0839278

(51) Int. Cl.
*C12R 1/01*     (2006.01)
*C12Q 1/527*    (2006.01)
*C12N 9/88*     (2006.01)

(52) U.S. Cl.
CPC .............. *C12N 9/88* (2013.01); *C12Q 1/527* (2013.01); *C12R 1/01* (2013.01)

(58) Field of Classification Search
CPC .............. C12N 9/88; C12R 1/01; C12Q 1/527
See application file for complete search history.

(56) References Cited

FOREIGN PATENT DOCUMENTS

| | | |
|---|---|---|
| CN | 1429913 A | 7/2003 |
| CN | 101886067 A | 11/2010 |
| CN | 102286448 A | 12/2011 |
| CN | 102864191 A | 1/2013 |
| CN | 102965362 A | 3/2013 |
| CN | 104593347 A | 5/2015 |
| WO | 98/03638 A1 | 1/1998 |
| WO | 2009059283 A1 | 5/2009 |

OTHER PUBLICATIONS

International Search Report for Corresponding PCT/CN2015/079704 dated Oct. 12, 2015.
Written Opinion for Corresponding PCT/CN2015/079704 dated Oct. 12, 2015.
Ma Xiao-lai; Yuan Ji-miang; Yuan Qin-sheng Purification of Flavobacterium heparinum heparinase I; (State Key Laboratory of Bio-reactor Engineering, East China University of Science and Technology Shanghai 200237, China) Jun. 30, 2005, pp. 40-42.
Chen Yin, Ye Feng-chun, Kuang Ying, Xing Xin-hui; Progress in the Study of Heparinases, Institute of Biochemical Engineering, Department of Chemical Engineering, Tsinghua University, Beijing 100084, China); Apr. 1, 2007; vol. 27 No. 8 2007, pp. 116-124.
Xiaolai Ma, Zunsheng Wang, Suxia Li, Qiong Shen, Qinsheng Yuan; Effect of CaCl sub 2 as activity stabilizer on purification of herparinase I from Flavobacterium heparinum; Journal of Chromatography B, 843 (2006) 209-215.

*Primary Examiner* — Delia M Ramirez
(74) *Attorney, Agent, or Firm* — Sanberg Phoenix & von Gontard PC

(57) ABSTRACT

Isolated and prepared heparinases SDhep I and SDhep II obtained from a bacterium *Sphingobacterium daejeonense* are heparin enzymes that have not been reported. The isolated and prepared enzymes were obtained by steps of bacterium fermentation, crude enzyme extraction, multi-step column chromatography and so on. A study in properties showed that the two enzymes are specific for enzymolysis of heparin and are expected to be used in low molecular weight heparins preparation or heparin quality testing.

9 Claims, 2 Drawing Sheets

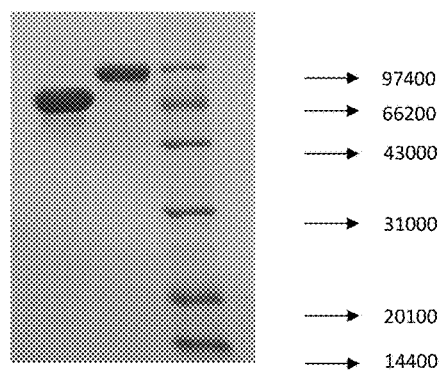
Figure 1: SDS-PAGE maps of SDhep I and SDhep II
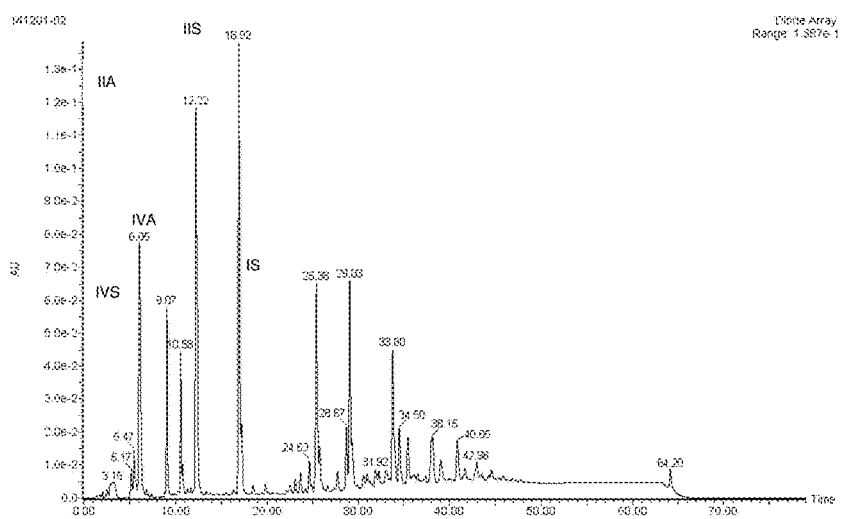
Figure 2. SAX-HPLC map of HEP product of SDhep I enzymolysis

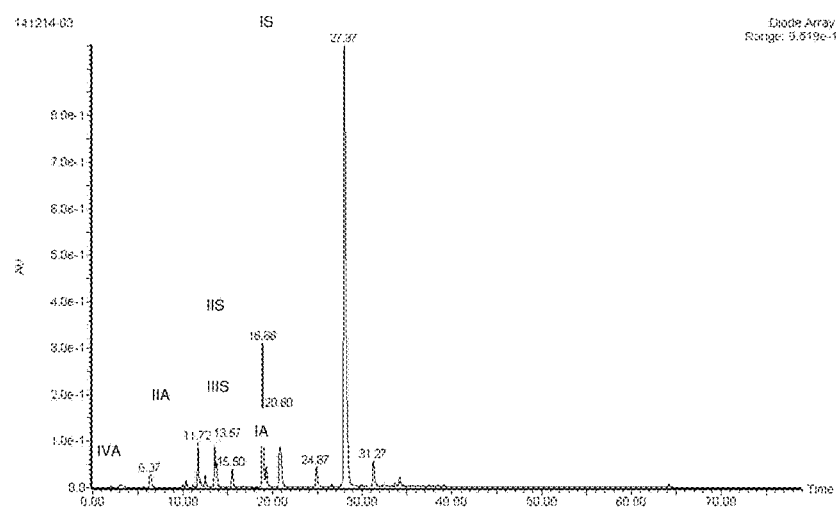
Figure 3. SAX-HPLC map of HEP product of SDhep II enzymolysis

HEPARINASES OBTAINED FROM *SPHINGOBACTERIUM DAEJEONENSE*, PREPARATION THEREFOR AND APPLICATION THEREOF

FIELD OF THE INVENTION

The present invention relates to novel isolated and prepared heparinases which have not been isolated, prepared or reported yet, and more particularly to two novel heparinases SDhep I and SDhep II derived from *Sphingobacterium daejeonense*, which have been prepared by bacterial fermentation, cell disruption and multi-step column chromatography, and to a preparation method of these two enzymes and their applications in the quality test of heparin and low molecular weight heparins.

PRIOR ART

Heparinases refer to a class of enzymes that can specifically cleave main chain glycosidic bonds of heparin and heparan, which have wide applications, such as removal of residual heparin in blood, preparation of low molecular weight heparins, study of heparin structure and heparin quality testing. Heparinases are originally found and isolated from *Flavobacterium heparinum* and also found in some microbial and animal tissues. There are more than 10 heparinases reported in academic papers, such as heparinases I, II, III found and isolated from *Flavobacterium heparinum* by Yang V. C.; a extracellularly-produced heparinase found from *Bacillus* BH100 (FERM BP-2613) by Robert W. Bellamy et al.; a heparinase found from *Fusarium oxysporum* HJ-15 by Wan-Seok Kim et al. [Carbohydrate Research, 2012, 359: 37-43].

The most widely studied and used heparinase are heparinase I, heparinase II and heparinase III, derived from *Flavobacterium heparinum*, which are monomeric protein with molecular weights of about 43, 78, 66 kDa, respectively and with isoelectric points of about 9.0. The discovery of heparinases has played an important role in structure study and quality testing of heparins, wherein the enzymes I, II, III derived from *Flavobacterium heparinum* have been used for heparin quality testing and low molecular weight heparins production.

The heparinases of the invention are novel isolated and prepared heparinases, which have not been reported yet, have different physicochemical properties from currently known heparinases, and have highly selective enzymatic cleavage sites, thus have a good application prospect.

SUMMARY OF INVENTION

The present invention provides two novel isolated and prepared intracellular heparinases SDhep I and SDhep II purified from a bacterial *Sphingobacterium daejeonense*, and describes a purification method and properties of the obtained enzymes. The molecular weight of SDhep I is 74692 Da, its Michaelis constant is 0.5738, and its isoelectric point is 5.64. The molecular weight of SDhep II is 94716 Da, its Michaelis constant is 0.0052 and its isoelectric point is 5.76. The two heparinases are the new Heparinases which have not been reported yet.

The present invention includes:
1. Bacteria strain: A strain (No. Z4-2) is isolated from the farmland soil of west of Chengguan Town, Yunmeng County, Hubei Province, China, which can produce heparinases when cultured with heparin-containing medium. The strain was cultured on a slant medium and stored at $-70°$ C., and was identified as *Sphingobacterium daejeonense* by the Guangdong Provincial Microbiological Analysis and Testing Center. This bacterium was reported in 2006 [Int J Syst Evol Microbiol., 2006, 56 (Pt 9): 2031-6.] but there is no report about heparinase production by the strain.

2. Preparation of Heparinases:

(1) Strain Fermentation and Crude Enzyme Solution Preparation of *Sphingobacterium daejeonense*:

Bacterium bodies are taken twice from a plate or a slope with an inoculating loop and inoculated into a seed medium and cultured for 1-2 days. Then the stain was inoculated into the secondary liquid seed medium with 5-20% inoculum amount and cultured for 1-2 days. Then the stain was inoculated into 2 L fermentation medium with 5-20% inoculum amount and cultured for 1-5 days. The bacterial solution was collected and centrifuged at 10,000 rpm for 15-30 minutes at 4° C. The precipitate was collected, suspended in Tris-HCl buffer, disrupted for 1-5 circles in a high pressure homogenizer at 800 bar at 4° C., and centrifuged for 30 min. Then the supernatant is taken and subjected to ammonium sulfate precipitation under ice bath, and the precipitated component with saturation of 35%-85% is collected. The precipitate was then dissolved in 100 mL Tris-HCl buffer and dialyzed overnight in the same buffer.

(2) Crude Enzyme Separation by Q Column:

The enzyme solution obtained in step (1) is loaded onto a Q column pre-equilibrated with a Tris-HCl buffer, then equilibrated with the same buffer, and then eluted with a linear gradient of 0-0.5 M NaCl in the same buffer. The effluent solution and the balance solution are collected in test tubes to detect heparinase activity; active fractions are collected and combined, being a heparinase not bound to Q column. The collected, combined and dialyzed fractions having heparinase activity from the eluent are a heparinase bound to the Q column.

(3) Purification of SDhep I Enzyme:

The heparinase not bound to the Q column obtained in step (2) is loaded onto a CS column pre-equilibrated with Tris-HCl buffer, then equilibrated with the same buffer and then eluted with a linear gradient of 0-0.5 M NaCl in the same buffer. The fractions with heparinase activity are collected and dialyzed. The dialyzed enzyme solution is loaded onto a SP column pre-equilibrated with Tris-HCl buffer, then equilibrated with the same buffer and then eluted with a linear gradient of 0-0.5 M NaCl in Tris-HCl buffer. The active fractions are collected and concentrated to 0.2 mL by an ultrafiltration centrifuge tube intercepting molecular weight of 30 kD. The concentrated enzyme solution is loaded onto a Sephadex G-100 column equilibrated with Tris-HCl buffer, then eluted with the same buffer, collected, combined and concentrated.

(4) Purification of SDhep II Enzyme:

The heparinase bound to Q column obtained in step (2) is loaded onto a CS column pre-equilibrated with a Tris-HCl buffer, then equilibrated with the same buffer, and then eluted with a linear gradient of a 0.1-0.6 M NaCl in the same buffer. The fractions with heparinase activity in the eluent solution are detected, collected, combined and dialyzed. The obtained enzyme solution is loaded onto a Q column pre-equilibrated with Tris-HCl buffer and eluted with 0.08 M NaCl in the same buffer. The active fractions are detected, collected, and loaded onto a CS column pre-equilibrated with Tris-HCl buffer, then equilibrated with the same buffer and then eluted with a linear gradient of 0-1 M NaCl in the same buffer. The active fractions were collected, combined and concentrated.

The Tris-HCl buffer described in each of steps (1), (2), (3) and (4) is Tris-HCl solution containing $CaCl_2$, pH 6.5-8.0. The concentration of Tris-HCl is preferably 10-50 Mm, most preferably 25 mM; the $CaCl_2$ content is preferably 1 to 50 mM, most preferably 10 mM; the preferred pH is in the range of 7.0 to 7.5, more preferably 7.0.

The Q column described in each of steps (2), (3) and (4) is Q-Sepharose Fast Flow, alternatively may be selected from Q-Sepharose Big Beads, Q-Sepharose XL, Q-Sepharose High Performance and other strong anion-exchange columns.

The CS column described in each of steps (3) and (4) is Cellufine Sulfate, alternatively may be CNBr-activated Sepharose CL-4B affinity column etc. which have been heparin-bound, and can bind heparinase.

The SP column described in step (3) is SP-Sepharose Fast Flow, alternatively may be selected from other strong cation-exchange columns.

The Sephadex G-100 column described in step (3) may alternatively be selected from other gel columns suitable for the separation and purification of 10-100 KDa proteins.

The determination of heparinase, heparan sulfate activity in the process is referred to a Chinese Patent Application No. 201110241260.4 "A Method for Producing Heparin *Flavobacterium* Heparinase I, II, III". Determination of protein content and enzyme purity is referred to [Carbohydrate Research, 2012, 359: 37-43]. Both are incorporated herein by reference.

The composition of the seed culture medium described in step (1) is also referred to CN 201110241260.4.

The composition (g/L) of the fermentation medium described in step (1) is 2 parts of tryptone, 8 parts of heparin, 5 parts of NaCl, 1 part of $(NH_4)_2SO_4$, 2.5 parts of $KH_2PO_4$, 0.5 part of $MgSO_4.7H_2O$, pH 7.0.

3. The Properties of the Heparinases
(1) The molecular weights of the heparinases SDhep I and SDhep II of the present invention determined by SDS-PAGE are about 74700 Da and 94700 Da respectively. The exact molecular weights determined by MALDI-TOF-MS mass spectrometry are 74692 Da for SDhep I and 94716 Da for SDhep II.
(2) The isoelectric points of heparinases SDhep I and SDhep II according to the present invention, measured by isoelectric focusing electrophoresis, are 5.64 and 5.76, respectively.
(3) The heparinases SDhep I and SDhep II according to the present invention both have optimum reaction pH of 8.0, with HEP or HS as a substrate.
(4) The optimal reaction temperature of the heparinase SDhep I, with HEP or HS as substrate, is 47° C. or 45° C., respectively. The optimum reaction temperature of SDhep II is 43° C., both for HEP and HS as the substrates.
(5) For the heparinases SDhep I and SDhep II in the present invention, $K^+$, $Mg^{2+}$, $Na^+$, $Mn^{2+}$ and $Ca^{2+}$ all have a promoting effect for enzyme activity, wherein $Ca^{2+}$ has the strongest effect, while $Cu^{2+}$, $Fe^{2+}$ and $Fe^{3+}$ have an inhibitory effect.

The present invention provides two heparinases derived from *Sphingobacterium daejeonense*, which are obtained by bacterial fermentation, cell disruption, ammonium sulfate precipitation and multi-step column chromatography isolation and purification. The physicochemical properties of the two heparinases SDhep I and SDhep II, including molecular weight and isoelectric point, are different from any of currently known heparinase. The two heparinases both can hydrolyze HEP and HS, and the resultant disaccharide having specific composition, respectively. The enzymes can be used to analyze the structures of heparins and analogues thereof, can be used for detection of heparin quality, and for preparation of low molecular weight heparins.

DESCRIPTION OF THE FIGURES

FIG. 1. SDS-PAGE maps of SDhep I and SDhep II enzymes.

FIG. 2. SAX-HPLC map of the product from enzymolysis of HEP by SDhep I.

FIG. 3. SAX-HPLC map of the product from enzymolysis of HEP by SDhep II

DETAILED DESCRIPTION OF THE INVENTION

The present invention is further illustrated by the following examples, but is not to be construed as limiting the present invention.

Example 1: Preparation of SDhep I a) *Sphingobacterium daejeonense* Strain Fermentation and Crude Enzyme Solution Preparation:

Bacterium bodies were taken twice from a plate or a slope with an inoculating loop and inoculated into 50 mL seed medium, shake-cultured at 30° C. and 150 rpm for 12 hours, and then inoculated into 200 mL secondary liquid seed medium with 10% inoculum mount and shake-cultured at 30° C. and 150 rpm for 24 hours and then fed into 2 L of the fermentation medium with 10% inoculum amount and shake-cultured at 30° C. and 150 rpm for 24 hours. 1 L of bacteria solution was taken out and centrifuged at 10,000 rpm for 30 min at 4° C. The precipitate was collected and suspended in 100 mL of 25 mM Tris-HCl buffer solution (containing 10 mM $CaCl_2$, pH 7.0) and disrupted in three cycles using a high pressure homogenizer at 4° C. and 800 bar, then centrifuged at 10,000 rpm for 30 min at 4° C., the supernatant being crude enzyme solution. Ammonium sulfate precipitation was carried out to collect precipitates with 35% to 85% of ammonium sulfate saturation. The precipitate was dissolved in 100 mL of Tris-HCl buffer and dialyzed overnight in the same buffer.

b) Q Column Separation:

The enzyme solution obtained in step a) was loaded onto a Q column with a size of 2.5×30 cm pre-equilibrated with 25 mM Tris-HCl (containing 10 mM $CaCl_2$, pH 7.0) buffer and then equilibrated with 3 column volumes in the same buffer. Loading effluent and equilibration effluent was examined for heparinase activity, and fractions with activity were collected and combined.

c) CS Column Purification:

The loading effluent and equilibration solution collected in step b) were loaded onto a CS column with a size of 2.5×30 cm pre-equilibrated with 25 mM Tris-HCl (containing 10 mM $CaCl_2$, pH 7.0) buffer. The column was equilibrated with 3 column volumes in the same buffer and then eluted with a linear gradient of 0-1 M NaCl in the buffer. The active fractions were collected and dialyzed in 2 L of 25 mM Tris-HCl containing 10 mM $CaCl_2$, pH 7.0 buffer overnight.

d) SP Column Purification:

The dialyzed enzyme solution obtained in step c) was loaded onto a SP column with a size of 2.5×30 cm pre-equilibrated with 25 mM Tris-HCl (containing 10 mM $CaCl_2$, pH 7.0) buffer, then equilibrated with 3 column volumes in the same buffer and then eluted with a linear gradient of 0-0.5 M NaCl in the buffer. The active fractions were collected and concentrated to 200 μL with ultrafiltration centrifuge tubes over 30 KD.

e) Sephadex G100 Column Purification:

The concentrated sample obtained in step d) was loaded onto a Sephadex G-100 column with a size of 1.0×100 cm pre-equilibrated with 25 mM Tris-HCl containing 10 mM $CaCl_2$, pH 7.0 buffer, and then eluted with the same buffer solution, wherein a peristaltic pump was used to control a flow rate of about 2 mL/h. The fractions were collected into tubes, 1 mL per tube, and determined the activity of the fractions. The fractions with enzyme activity were collected and concentrated to 200 μL by 30 KD ultrafiltration centrifuge tub, and placed in a 1.5 mL EP tube. 300 μL of a buffer of 25 mM Tris-HCl (containing 10 mM $CaCl_2$, pH 7.0) was added and then 500 μL of glycerol were added to a volume of 1 mL. The enzyme activity and protein content for each step of the purification procedure are shown in the following table.

TABLE 1

Enzyme activity and protein content for each step in SDhep I purification

| SDhep I purification steps | Total volume (mL) | Total protein (mg) | HEP enzyme activity (IU/mL) | Total activity (IU) | Specific activity (IU/mg) | purification multiple | Yield (%) |
|---|---|---|---|---|---|---|---|
| Crude enzyme | 150 | 76.65 | 2.41 | 361.5 | 4.72 | / | / |
| Thiamine precipitation | 135 | 37.80 | 2.60 | 351.0 | 9.29 | 1.97 | 97.10 |
| Q column | 135 | 12.82 | 1.22 | 164.7 | 12.85 | 2.72 | 45.56 |
| CS column | 75 | 2.47 | 1.38 | 103.5 | 41.90 | 8.88 | 28.63 |
| SP column | 62 | 0.81 | 1.03 | 63.9 | 78.84 | 16.70 | 17.67 |
| Sephadex G-100 | 1 | 0.278 | 50.6 | 50.6 | 182.01 | 38.56 | 14.00 |

Example 2: Study on the Properties of SDhep I

The molecular weight of SDhep I was about 74700 Da by SDS-PAGE, as shown in FIG. 1, and its exact molecular weight was 74692 Da by MALDI-TOF-MS mass spectrometry analysis.

The isoelectric point of SDhep I was 5.64 by isoelectric focusing electrophoresis.

Initial enzyme reaction rates were determined under various substrate concentrations to obtain Michaelis constant, the Michaelis constant of the SDhep I were 0.5738 and 0.0418 respectively as HEP or HS being the substrate.

Activity of heparinase SDhep I was determined as HEP or HS being the substrate respectively, and substrate pH being 5.0, 5.5, 6.0, 6.5, 7.0, 7.5, 8.0, 8.5 and 9.0 respectively. The results showed that pH range with enzyme activity was 6.5-9.5 as HEP being the substrate, and the optimum pH was 8.0. As HS being the substrate, pH range with enzyme activity was 5.5-9.0, and the optimum pH was 8.0.

Activity of heparinase SDhep I was determined as HEP or HS being the substrate respectively, and substrate temperatures being 25, 27, 29, 31, 33, 35, 37, 39, 41, 43, 45, 47 and 49° C., respectively. The results showed that the optimal temperature was 47° C. as HEP being the substrate, and the optimum temperature was 45° C. as HS being the substrate.

Effects of metal ion species on SDhep I: effect on SDhep I of adding 10 mM $Mg^{2+}$, $Mn^{2+}$ and $Ca^{2+}$, $Na^+$, $K^+$, $Mg^{2+}$, $Cu^{2+}$, $Fe^{2+}$, $Fe^{3+}$, or $Mn^{2+}$ respectively in the substrate HEP or HS, with 25 mM Tris-HCl (pH7.0) as a buffer, was tested, taking no addition of any metal ions as a blank control group. The results showed that $K^+$, $Mg^{2+}$, $Na^+$, $Mn^{2+}$ and $Ca^{2+}$ improved enzyme activity, wherein $Ca^{2+}$ had the best effects on the improvement of enzyme activity, largely promoted enzyme activity. $Mg^{2+}$ and $Na^+$ had the obviously improvement for enzyme activities. However, $Cu^{2+}$, $Fe^{2+}$ and $Fe^{3+}$ had an inhibitory effect, which inactivated the enzyme.

Effects of metal ion concentrations on SDhep I: the effect of $Mg^{2+}$, $Na^+$ or $Ca^{2+}$ at 0, 1, 10, 50, 100, 500 and 1000 mM, respectively on the enzyme activity was examined, as HEP or HS being the substrate. The results showed that the optimum concentration of $Mg^{2+}$ for improving the activity of SDhep I was 100 mM as HEP or HS being the substrate. As HEP being the substrate, the optimum concentration of $Na^+$ was 500 mM. As HS being the substrate, the optimum concentration of $Na^+$ for SDhep I was 50 mM. The optimum concentration of $Ca^{2+}$ was 100 mM as HEP or HS being the substrate.

Effects of denaturants on SDhep I: effect of denaturants on heparinase SDhep I activity was examined taking $H_2O_2$, acetonitrile, SDS, guanidine hydrochloride or urea as a denaturant respectively, the respective concentrations being 1 mM and 10 mM for $H_2O_2$, 1% and 10% for acetonitrile, 1% SDS, 1 M guanidine hydrochloride and 1 M urea, and setting a blank control group without any denaturing agent. In the presence of the above denaturing agent, 1% and 10% acetonitrile, and 1 M urea had a little effect on SDhep I, while 1 mM and 10 mM $H_2O_2$, 1% SDS, and 1M guanidine hydrochloride had significant inhibitory effect on SDhep I.

Example 3: Study on Specificity of Products from Enzymolysis of HEP by SDhep I a) study on specificity of SDhep I substrate: activity of SDhep I was determined taking heparin (HEP), heparan sulfate (HS), chondroitin sulfate (CS) or dermatan sulfate (DS) as the substrate respectively. It is found that there was no enzyme activity with CS or DS being the substrate; and there was enzyme activity with HEP or HS being the substrate, and their activity ratio was about HEP:HS=1:1.3.

b) disaccharide composition after enzymolysis of HEP by SDhep I: 3 IU of SDhep I (with heparin being substrate) was added to 50 mg of heparin, volume being balanced to 500 μL with 25 mM Tris-HCl buffer containing 10 mM CaCl$_2$, pH 7.0, and hydrolyzed at 37° C. for 24 h, then placed in a 100° C. water bath for 5 min for inactivation. The sample was subjected to liquid phase analysis for disaccharide composition, and the results were shown in FIG. 2. The main products after hydrolysis of HEP by SDhep I were IVA, IVS, IIA, IIS and IS, in which IIA and IIS accounted for 15.35% and 12.2% and peak area of IS only accounted for 5.29%. There were numerous types of tetrasaccharides components in addition to the above several disaccharides.

Example 4: Preparation of SDhep II a) bacteria fermentation and crude enzyme preparation were the same as in Example 1.
b) the step of crude enzyme separation by Q column was the same as in Example 1. After equilibrated with buffer of 3 column volumes, the sample was eluted with a linear gradient of 0-0.5 M NaCl in the buffer. The eluent active fractions were collected and dialyzed overnight.
c) CS column Purification: the enzyme solution obtained in step b) was loaded onto a CS column pre-equilibrated with 25 mM Tris-HCl buffer (containing 10 mM CaCl$_2$, pH 7.0), then equilibrated with the same buffer of 3 column volumes, and then eluted with a linear gradient of 0-1 M NaCl in the buffer, and the active fractions were collected and dialyzed overnight with 2 L volume of 25 mM Tris-HCl buffer (containing 10 mM CaCl$_2$, pH 7.0).
d) Q column Purification: the enzyme solution obtained in step c) was loaded onto a Q column pre-equilibrated with 25 mM Tris-HCl buffer (containing 10 mM CaCl$_2$, pH 7.0), and then eluted with 800 mL of 0.080 M NaCl in the same buffer. The eluent active fractions were collected.
e) CS column Purification: an equal volume of buffer was added to the fractions with enzyme activity collected in step d) and the mixture was loaded onto CS column pre-equilibrated with 25 mM Tris-HCl (containing 10 mM CaCl2, pH 7.0), then equilibrated with the same buffer of 3 column volumes, and then eluted with a linear gradient of 0-1M NaCl in the same buffer. The active fractions were collected and subjected to a SDS-PAGE. The active fractions showing single band in electrophoresis was collected and concentrated to 200 μL with 30 KD ultrafiltration centrifuge tube. The concentration was taken out and placed into a 1.5 mL EP tube, adding 300 μL of 25 mM Tris-HCl buffer (containing 10 mM CaCl$_2$, pH 7.0), then adding 500 μL glycerol and then balancing volume to 1 mL. The enzyme activity and protein content for each step of the purification procedure are shown in the following table.

TABLE 2

The enzyme activity and protein content in SDhep II purification

| SDhep II purification step | Total volume (mL) | Total protein (mg) | HEP enzyme activity (IU/mL) | Total vitality (IU) | Specific Activity (IU/mg) | Purification factor | Yield (%) |
|---|---|---|---|---|---|---|---|
| Crude enzyme | 150 | 76.65 | 2.41 | 361.5 | 4.72 | / | / |
| Thiamine precipitation | 135 | 37.80 | 2.60 | 351.0 | 9.29 | 1.97 | 97.10 |
| Q column | 54 | 10.69 | 2.82 | 152.2 | 14.25 | 3.02 | 42.12 |
| CS column | 120 | 3.96 | 0.82 | 98.4 | 24.85 | 5.26 | 27.22 |
| Q column II | 300 | 2.10 | 0.18 | 54.0 | 25.71 | 5.45 | 14.94 |
| CS column II | 1 | 0.29 | 29.6 | 29.6 | 102.07 | 21.62 | 8.19 |

Example 5: Study on Properties of SDhep II

The results were shown in FIG. 1, the molecular weight of SDhep II was about 94700 Da by SDS-PAGE analysis, and its exact molecular weight was 94716 Da according to MALDI-TOF-MS mass spectrometry analysis.

The isoelectric point of SDhep II was 5.76 by isoelectric focusing electrophoresis analysis.

Initial enzyme reaction rates were determined under various substrate concentrations to obtain Michaelis constant. The Michaelisemi constant of the SDhep II was determined to be 0.0052 and 1.6618 respectively for HEP or HS being the substrate.

Activity of heparinase SDhep II was determined as HEP or HS being the substrate and substrate pH being 5.0, 5.5, 6.0, 6.5, 7.0, 7.5, 8.0, 8.5 and 9.0 respectively. The results showed that the pH range with activity was 6.5-9.0 as HEP being the substrate, and the optimum pH was 8.0. As HS being the substrate, the pH range was 6.5-9.0, and the optimum pH was 8.0.

Activity of heparinase SDhep II was determined as HEP or HS being the substrate and substrate temperature being 25, 27, 29, 31, 33, 35, 37, 39, 41, 43, 45, 47 and 49° C., respectively. The results showed that the optimal temperature was 47° C. as HEP being the substrate, and the optimum temperature was 43° C. as HS being the substrate.

Effects of metal ion species on SDhep II: effects on enzyme SDhep II of adding 10 mM $Mg^{2+}$, $Mn^{2+}$ and $Ca^{2+}$, $Na^+$, $K^+$, $Mg^{2+}$, $Cu^{2+}$, $Fe^{2+}$, $Fe^{3+}$, and $Mn^{2+}$ respectively to substrate HEP or HS respectively were examined, with 25 mM Tris-HCl (pH7.0) as a buffer, taking no addition of any metal ions as a blank control group. The results showed that $K^+$, $Mg^{2+}$, $Na^+$, $Mn^{2+}$ and $Ca^{2+}$ improved the enzyme activity, wherein $Ca^{2+}$ had the best effects for the improvement of enzyme activity, largely promoted the enzyme activity. $Mg^{2+}$ and $Na^+$ had the obviously improvement for enzyme activities. However, $Cu^{2+}$, $Fe^{2+}$ and $Fe^{3+}$ had an inhibitory effect, which inactivated the enzyme.

Effects of metal ion concentration on SDhep II: effect of $Mg^{2+}$, $Na^+$ or $Ca^{2+}$ at 0, 1, 10, 50, 100, 500 and 1000 mM, respectively on enzyme SDhep II activity was examined, with HEP or HS being the substrate. The results showed that the optimum concentration of $Mg^{2+}$ for improving the activity of SDhep II was 100 mM as HEP or HS being the substrate. As HEP or HS being the substrate, the optimum concentration of $Na^+$ for improving the activity of SDhep II was 100 Mm and 50 mM. The optimum concentration of $Ca^{2+}$ for improving the activity of SDhep II was 100 mM or 50 mM.

Effects of denaturants on SDhep II: effect of denaturants on heparinase SDhep II activity was examined taking $H_2O_2$, acetonitrile, SDS, guanidine hydrochloride or urea as a denaturant respectively, the respective concentrations being 1 mM and 10 mM for $H_2O_2$, 1% and 10% for acetonitrile, 1% SDS, 1 M guanidine hydrochloride and 1 M urea, and setting a blank control group without any denaturing agent.

In the presence of the above denaturing agent, 1% and 10% acetonitrile, and 1 M urea had a little effect on SDhep II, while 1 mM and 10 mM $H_2O_2$, 1% SDS, and 1M guanidine hydrochloride had significant inhibitory effect on SDhep II.

Example 6: Study on Specificity of Products from Enzymolysis of HEP by SDhep II a) study on specificity of SDhep II substrate: activity of SDhep II was determined taking heparin (HEP), heparan sulfate (HS), chondroitin sulfate (CS) or dermatan sulfate (DS) as the substrate respectively. The results showed that there was no enzyme activity with CS or DS being the substrate; and there was enzyme activity with HEP or HS being the substrate, and their activity ratio was about HEP:HS=1:3.5.

b) disaccharide composition analysis after enzymolysis of HEP by SDhep II: 3 IU of SDhep II (with heparin being substrate) was added to 50 mg of heparin, volume being balanced to 500 μL with 25 mM Tris-HCl buffer (containing 10 mM $CaCl_2$, pH 7.0), hydrolyzed at 37° C. for 24 h, then placed in a 100° C. water bath for 5 min for inactivation. The sample was subjected to liquid phase analysis for disaccharide composition; the results were shown in FIG. 3. The main products after hydrolysis of HEP by SDhep II were IIS and IS, in which IS was of majority and accounted for 56.39%. Compared with SDhep I, enzymatic products of SDhep II was less and its enzymatic hydrolysis was more completely, very different from the products by SDhep I. Therefore, SDhep I and SDhep II were two heparin enzymes with very different enzymatic properties, which have potential application value in heparin quality detection and low molecular weight heparins preparation.

The invention claimed is:

1. A method for obtaining a purified heparinase with a molecular weight of 74,692 Da and an isoelectric point of 5.64 from a *Sphingobacterium daejeonense* bacterium, comprising the steps of:
   (a) inoculating a *Sphingobacterium daejeonense* strain on a slant medium;
   (b) culturing the strain obtained in step (a) in a seed culture medium for 1-2 days, followed by culturing the strain in a secondary liquid seed medium for 1-2 days, and culturing in a fermentation medium for 1-5 days, thereafter collecting cells;
   (c) suspending the cells obtained in step (b) and disrupting said cells to obtain a cell supernatant by centrifugation,
   (d) conducting an ammonium sulfate precipitation of the cell supernatant of step (c) in an ice bath, collecting a precipitated component with 35%-85% saturation, dissolving the precipitate in a Tris-HCl buffer and dialyzing it to obtain an enzyme solution;
   (e) loading the enzyme solution obtained in step (d) onto a Q-Sepharose column and collecting the fractions with heparinase activity from the Q-Sepharose column effluent;
   (f) loading the fractions with heparinase activity obtained from step (e) onto a CS column, wherein the CS column is a Cellufine Sulfate affinity column or a heparin-bound affinity column, and collecting fractions with heparinase activity from the CS column effluent;
   (g) loading the fractions with heparinase activity obtained from step (f) onto an SP column, wherein the SP column is a strong cation-exchange column, and collecting fractions with heparinase activity from the SP column effluent; and
   (h) loading the fractions with heparinase activity obtained from step (g) onto a Sephadex G-100 column, collecting the fractions with heparinase activity from the Sephadex G-100 column effluent, combining said fractions and concentrating the fractions to obtain the purified heparinase having a molecular weight of 74,692 Da and an isoelectric point of 5.64.

2. The method of claim 1, wherein the Tris-HCl buffer is a $CaCl_2$-containing Tris-HCl buffer at a pH of 6.5-8.0, wherein the Tris-HCl concentration of the Tris-HCl buffer is 10-50 mM and the $CaCl_2$ concentration is 1-50 mM.

3. The method of claim 1, wherein the Q-Sepharose column is a Q-Sepharose Fast Flow strong anion-exchange column.

4. The method of claim 1, wherein the CS column is a Cellufine Sulfate affinity column.

5. The method of claim 1, wherein the SP column is an SP-Sepharose Fast Flow strong cation-exchange column.

6. A method for obtaining a purified heparinase with a molecular weight of 94,716 Da and an isoelectric point of 5.76 from a *Sphingobacterium daejeonense* bacterium, comprising the steps of:
   (a) inoculating a *Sphingobacterium daejeonense* strain on a slant medium;
   (b) culturing the strain obtained in step (a) in a seed culture medium for 1-2 days, followed by culturing the strain in a secondary liquid seed medium for 1-2 days, and culturing in a fermentation medium for 1-5 days, thereafter collecting cells;
   (c) suspending the cells obtained in step (b) and disrupting said cells to obtain a cell supernatant by centrifugation,
   (d) conducting an ammonium sulfate precipitation of the cell supernatant of step (c) in an ice bath, collecting a precipitated component with 35%-85% saturation, dissolving the precipitate in a Tris-HCl buffer and dialyzing it to obtain an enzyme solution;
   (e) loading the enzyme solution obtained in step (d) onto a Q-Sepharose column, collecting the fractions with heparinase activity from the Q-Sepharose column effluent, combining said fractions and dialyzing the combined fractions;
   (f) loading the fractions with heparinase activity obtained from step (e) onto a CS column, wherein the CS column is a Cellufine Sulfate affinity column or a heparin-bound affinity column, collecting fractions with heparinase activity from the CS column effluent, combining said fractions and dialyzing the combined fractions;
   (g) loading the fractions with heparinase activity obtained from step (f) onto a Q-Sepharose column, and collecting fractions with heparinase activity from the Q-Sepharose column effluent; and
   (h) loading the fractions with heparinase activity obtained from step (g) onto the CS column of step (f), collecting the fractions with heparinase activity from the CS column effluent, combining the fractions and concentrating the fractions to obtain the purified heparinase having a molecular weight of 94,716 Da and an isoelectric point of 5.76.

7. The method of claim 6, wherein the Tris-HCl buffer is a $CaCl_2$-containing Tris-HCl buffer at a pH of 6.5-8.0, wherein the Tris-HCl concentration of the Tris-HCl buffer is 10-50 mM and the $CaCl_2$ concentration of the Tris-HCl buffer is 1-50 mM.

8. The method of claim 6, wherein the Q-Sepharose column is a Q-Sepharose Fast Flow strong anion-exchange column.

9. The method of claim 6, wherein the CS column is a Cellufine Sulfate affinity column.

\* \* \* \* \*